US006991787B1

(12) United States Patent
Greenberger et al.

(10) Patent No.: US 6,991,787 B1
(45) Date of Patent: Jan. 31, 2006

(54) METHODS OF PREPARING BONE MARROW STROMAL CELLS FOR USE IN GENE THERAPY

(75) Inventors: Joel S. Greenberger, Sewickley, PA (US); David R. Hurwitz, Acton, MA (US)

(73) Assignee: ALG Company, Marlborough, MA (US)

( * ) Notice: Subject to any disclaimer, the term of this patent is extended or adjusted under 35 U.S.C. 154(b) by 0 days.

(21) Appl. No.: 09/633,093

(22) Filed: Aug. 4, 2000

Related U.S. Application Data

(63) Continuation of application No. 09/107,051, filed on Jun. 30, 1998, now abandoned, which is a continuation of application No. 08/581,053, filed on Dec. 29, 1995, now abandoned.

(51) Int. Cl.
*A01N 63/00* (2006.01)
*A01N 1/02* (2006.01)
*A61K 48/00* (2006.01)
*C12N 5/02* (2006.01)
*C12N 15/09* (2006.01)

(52) U.S. Cl. ................. 424/93.21; 424/43.1; 424/93.2; 435/1.3; 435/2; 435/325; 435/455

(58) Field of Classification Search ................ 424/934; 435/172.1
See application file for complete search history.

(56) References Cited

U.S. PATENT DOCUMENTS

| | | | |
|---|---|---|---|
| 4,117,881 A | 10/1978 | Williams et al. | |
| 4,721,096 A | 1/1988 | Naughton et al. | .......... 128/1 R |
| 5,399,346 A * | 3/1995 | Anderson et al. | ........ 424/93.21 |
| 5,399,493 A | 3/1995 | Emerson et al. | |
| 5,591,625 A | 1/1997 | Gerson et al. | |
| 5,817,453 A * | 10/1998 | Brinster | ...................... 435/1.1 |
| 5,849,287 A * | 12/1998 | Greenberger et al. | .... 424/93.21 |
| 5,993,801 A * | 11/1999 | Greenberger et al. | .... 424/93.21 |
| 6,020,188 A * | 2/2000 | Newman | .................. 435/320.1 |
| 6,258,354 B1 * | 7/2001 | Greenberger | ............ 424/93.21 |
| 6,326,198 B1 * | 12/2001 | Emerson et al. | ............ 435/373 |

FOREIGN PATENT DOCUMENTS

| | | |
|---|---|---|
| EP | 0 381 490 A2 * | 2/1990 |
| EP | 0 381 490 A2 | 8/1990 |
| WO | WO 91/18620 | 12/1991 |
| WO | PCT/US95/16991 | 12/1995 |

OTHER PUBLICATIONS

Yamada et al, Nagoya J Med Sci 1982;44:117-31.*
Rowley, J Hematotherapy 1992;1:233-250.*
Hacker et al, Proc Am Asso Can Res 1975;16:66.*
Ponnazhagan et al, J Virol 1997;71:8262-7.*
Valerio et al, Nucleic Acids Res. 1988;16:10083-97.*
Graubert et al, Nucleic Acids Res. 1998;26:2849-58.*
R Lobb et al., Biochemical and Biophysical Res. Comm., "Expression and Functional Characterization of a Soluble Form of Vascular Cell Adhesion Molecule 1," Aug. 1991, vol. 178, No. 3, pp. 1498-1504.*
Lozier et al. (1994) Human Gene Therapy 5:313-322.*
Boswell et al., 1983, Exp. Hematol. 11:315-323.
Brunner et al., 1993, Blood 81:631-638.
Gilabert et al., 1994, Eur. J. Haematol. 53: 93-99.
Kimura et al., 1988, Br. J. Hematol. 69:9-12.
Motta et al., 1993, Bone Marrow Trans. 12:177.
Nicol et al., 1995, Blood 86(Supp. 1):120s, Abstract No. 469.
Sorger et al., 1995, In Vitro Cell. Dev. Biol. —Animal 31:671-683.
Anklesaria et al., "Engraftment of clonal bone . . . hematopoietic recovery from total body irradiation", *Proc. Natl. Acad. Sci.*, USA, 84:7681-7685 (Nov. 1987).
Anklesaria et al., Expression of a Selectable . . . Bone Marrow Cultures, *Experimental Hematology*, 15:195-202, (1987).
Ding et al., "The Stromal Cell as a Vehicle for Ex Vivo Gene Transfer", *Blood*, 86:10 Suppl. 1, p. 409A, Abstract 1625, (1995).
Drize et al., "Gene Therapy Model . . . Hematopoietic Microenvironment", *Leukemia*, 6(Supp.3):174S-175S, (1992).
Foley et al., "Effective Cytokine . . . Adenoviral Vectors", *Journal Cellular Biochemistry*, 21A:406, Abstract C6-415, (1995).
Huss et al., Homing and Immunogenicity . . . MHC Class II Genes, *Cell Transplantation*, 4:483-491 (1995).
Keating, "Bone marrow stromal cell transplantation", *Bone Marrow Transplantation*, 15(Supp.1):S9-S14, (1995).
Lazarus et al., "Ex vivo expansion and . . . implications for therapeutic use", *Bone Marrow Tranplantation*, 16:557-564, (1995).
Li et al., Retroviral-mediated gene . . . in vivo survival in SCID mice, *Eur. J. Haematol*, 55:302-306 (1995).
Luskey et al. Gene Transfer into . . . and Bone Marrow Stromal Cells, *Ann. N.Y. Acad. Sci.*, 612:398-406, (1990).
Roux et al., "Retrovirus-mediated gene . . . mouse bone marrow stromal cells", *Oncogene*, 6:2155-2160, (1991).

* cited by examiner

*Primary Examiner*—Q. Janice Li
(74) *Attorney, Agent, or Firm*—Synnestvedt & Lechner LLP

(57) ABSTRACT

This invention relates to sequential methods of cryopreserving bone marrow stromal cells that are transfected and used for gene therapy by transplantation. These methods include the following steps in various orders: obtaining the cells, expanding the cells in culture, transfecting the cells, and cryopreserving the cells. With these methods, populations of bone marrow stromal cells can be acquired that are large enough to be useful in a number of therapies. Further, these large populations can be stored for extended periods of time for immediate use when needed.

14 Claims, 5 Drawing Sheets

* Plasma (ng/ml) / In Vitro (total µg expression capacity / 24 hours) x kg Dog Weight x 100

METHODS OF PREPARING BONE MARROW STROMAL CELLS FOR USE IN GENE THERAPY

This application is a continuation of U.S. Ser. No. 09/107,051, filed on Jun. 30, 1998, (now abandoned) which is a continuation of U.S. Ser. No. 08/581,053, filed on Dec. 29, 1995 (now abandoned), both of which are incorporated herein by reference in their entirety.

BACKGROUND OF THE INVENTION

This invention relates to methods of preparing bone marrow stromal cells for use in ex vivo gene therapy.

Bone marrow is a complex and dynamic organ system comprised of hematopoietic cells, bone marrow stromal cells, and extracellular matrix. Pluripotent stem cells within the bone marrow proliferate and differentiate into numerous cell types including erythrocytes and leukocytes. It has been known for some time that association between stem cells and stromal cells is critical for this process. Studies in cell culture have shown that a layer of adherent stromal cells must be established before hematopoietic stem cells can grow and differentiate.

Bone marrow stromal cells are a heterogeneous population of cells that are defined by their morphology and function. In cell culture, they have a characteristic, spindle-shaped morphology and secrete growth factors and components that form an extracellular matrix. Stromal cells have been shown to divide in culture in response to epidermal growth factor (EGF; Kimura et al., 1988, Br. J. Hematol. 69:9–12), platelet derived growth factor (PDGF; Kimura et al., supra), and basic fibroblast growth factor (bFGF; Kimura et al., supra; Oliver et al., 1990, Growth Factors, 3:231–236).

Bone marrow and other biological substances can be frozen according to precalculated time and temperature curves (see, e.g., U.S. Pat. Nos. 4,107,937 and 4,117,881). Cryopreserved materials can be stored for extended periods of time with little degradation (Motta, M. R., (1993), Bone Marrow Trans. 12(2):177). Further, U.S. Pat. No. 4,963,489 indicates that when a suspension of fresh bone marrow and blood is mixed with cryoprotectants and frozen using computerized cryotechnological equipment, 90% of the cells remain viable when thawed. See also, Boswell et al., 1983, Exp. Hematol. 11:315–323; Gilabert et al., 1994, Eur. J. Haematol. 53:93–99; and Rowley, 1992, J. Hematother. Fall:1(3):233–250.

Bone marrow transplantation is a promising therapy for a number of diseases that involve hematopoietic cells. Transplantation can serve to replace cells that have been damaged by an intrinsic disease, such as an anemia, or in instances where hematopoietic cells have been destroyed by chemotherapy or radiation therapy. Transplantation can be autologous, i.e., the patient can serve as his or her own donor. Alternatively, a patient could receive bone marrow from a histocompatible donor. To date, however, conditions for preserving bone marrow, particularly bone marrow stromal cells, which could be used in numerous gene therapies, have not been optimized.

A major obstacle to gene therapies based on the modification of stromal cells is the procurement and sustained availability of therapeutically useful numbers of stromal cells. Consequently, despite the success of bone marrow transplantation, gene therapies that require successful transplantation of bone marrow stromal cells have not yet been realized.

SUMMARY OF THE INVENTION

This invention relates to sequential methods of expanding and cryopreserving bone marrow stromal cells that are transfected and used for gene therapy. The invention is based on the discovery that bone marrow stromal cells can be cryopreserved and then transfected, or transfected and then cryopreserved, and yet still maintain the ability to effectively secrete a desired polypeptide. The cells are plated and expanded according to a particular regimen in complete bone marrow stromal cell medium. With these methods, populations of bone marrow stromal cells can be acquired that are large enough to be useful in a number of therapies. Further, these large populations can be stored for extended periods of time for immediate use when needed.

In general, the invention features a method of preparing bone marrow stromal cells for implantation for gene therapy. The method includes the steps of: (a) obtaining bone marrow stromal cells; (b) culturing the stromal cells to obtain an expanded number of cultured stromal cells; (c) transfecting cultured stromal cells with an exogenous gene to obtain transfected stromal cells; and (d) cryopreserving the transfected stromal cells until implantation.

In another aspect, the method includes the steps of: (a) obtaining bone marrow stromal cells; (b) culturing the stromal cells to obtain an expanded number of cultured stromal cells; (c) cryopreserving the cultured stromal cells; (d) thawing the cryopreserved stromal cells; and (e) transfecting the thawed stromal cells with an exogenous gene prior to implantation.

In another aspect, the method includes the steps of: (a) obtaining bone marrow cells, e.g., from a primary aspirate of bone marrow; (b) cryopreserving the bone marrow cells; (c) thawing the cryopreserved bone marrow cells; (d) culturing the thawed bone marrow cells to obtain an expanded number of cultured stromal cells; and (e) transfecting the cultured stromal cells with an exogenous gene prior to implantation.

In each of these methods, the bone marrow stromal cells can be obtained from bone marrow, e.g., by a primary bone marrow aspirate, a core sample, or by scrapings from one or more bones, from a vertebrate, living or not, e.g., a primate such as a baboon or a human, or mammals in general including dogs, pigs, and cows, or other animals, or can be obtained from bones removed from a vertebrate.

The exogenous gene preferably encodes a secreted peptide such as a serum protein, a blood clotting factor, e.g., factor VIII or factor IX, a cytokine, a lymphokine, a growth factor, e.g., human growth hormone, a peptide hormone, a lipid binding protein, a metabolic enzyme, an antibacterial peptide, an antimicrobial peptide, an antifungal peptide, or a neurotransmitter. The exogneous gene can also encode a cell surface molecule, e.g., V-CAM-1, I-CAM-1, N-CAM, or V-LAM.

In these methods, the culturing or expanding steps can include the steps of: introducing the stromal cells into a vessel pre-coated on an inner surface with a gelatin, e.g., 1.0 percent gelatin in water, and containing a culture medium including an acidic fibroblast growth factor ("aFGF") polypeptide; and expanding the stromal cells in the culture medium under conditions and for a time sufficient to obtain an increased number of bone marrow stromal cells. In these culturing methods, the culture medium further preferably includes at least 0.05 units/ml of a heparin polypeptide. The inner surface of the vessel additionally can be precoated with fetal bovine serum prior to introducing the bone marrow stromal cells.

In particular, the culture medium used in these methods can include 1.0 to 50.0 percent by volume fetal bovine serum, 0.01 to 100.0 ng/ml aFGF polypeptide, and 0.05 to 100 units/ml heparin polypeptide. In a specific embodiment, the culture medium includes 16.0 percent by volume fetal bovine serum, 1.0 ng/ml aFGF polypeptide, and 5.0 units/ml heparin polypeptide.

The expansion step of the culturing method preferably includes the steps of: (i) removing culture medium and non-adherent cells from the vessel; (ii) adding an amount of fresh culture medium to the vessel; (iii) removing culture medium and non-adherent cells from the vessel and centrifuging the medium and non-adherent cells to form a pellet of non-adherent cells; (iv) resuspending the pellet of non-adherent cells in an amount of culture medium taken from the vessel to form a non-adherent cell mixture; and (v) returning the non-adherent cell mixture to the vessel.

As used herein, an "aFGF polypeptide" is any polypeptide that has an amino acid sequence that is the same as, or substantially identical to, all or a portion of the naturally occurring aFGF protein and which has substantially the same function as the natural or full-length recombinant aFGF as described herein with respect to bone marrow stromal cells. Thus, the term includes recombinant aFGF (e.g., as manufactured by Life Technologies, Inc., Grand Island, N.Y.; #13241-013), "aFGF analogs," i.e., mutant forms of aFGF, and natural or synthetic polypeptide fragments of the full-length aFGF protein and analogs, as long as these analogs and fragments have substantially the same function as natural or full-length recombinant aFGF with respect to bone marrow stromal cells as described herein. These analogs and fragments can easily be tested for their function by using the culture methods described below. Acidic FGF analogs and fragments that do not provide at least $10^7$ cells with these methods are not within the present invention.

Similarly, a "heparin polypeptide" is any polypeptide that has an amino acid sequence that is the same as, or substantially identical to, all or a portion of the naturally occurring heparin protein and which has substantially the same function as the natural heparin as described herein with respect to bone marrow stromal cells. Thus, the term includes natural heparin or chemically modified natural heparin, e.g., sodium heparin (ElkinsSinn, Inc., Cherry Hill, N.J.), recombinant heparin, "heparin analogs," i.e., mutant forms of heparin, and natural or synthetic polypeptide fragments of the full-length heparin protein and analogs, as long as these analogs and fragments have substantially the same function as natural heparin with =respect to bone marrow stromal cells as described herein. The heparin function can be assayed using the culture methods described below.

By "polypeptide" is meant any chain of amino acids, regardless of length or post-translational modification, e.g., glycosylation, phosphorylation, or chemical modification, and thus includes natural and synthetic peptides and proteins.

By "mutant form" of aFGF or heparin is meant a polypeptide that includes any change in the amino acid sequence compared to the naturally occurring protein, as long as the mutant form has substantially the same function as the natural or full-length recombinant protein as described herein with respect to bone marrow stromal cells. These changes can arise, e.g., spontaneously by chemical energy, e.g., X-ray, or by other forms of mutagenesis, by genetic engineering, or as a result of mating or other forms of exchange of genetic information encoding the aFGF polypeptide. Mutations can include, for example, substitutions, deletions, insertions, inversions, translocations, or duplications. The mutations are preferably conservative substitutions, e.g., substitutions within the following groups: glycine alanine; valine, isoleucine, leucine; aspartic acid, glutamic acid, asparagine, glutamine; serine, threonine; lysine, arginine; and phenylalanine, tyrosine.

The term "identical" as used herein in reference to polypeptides, refers to the amino acid sequence similarity between two polypeptides. When an amino acid position in both of the polypeptides is occupied by identical amino acids, then they are identical at that position. Thus, by "substantially identical" is meant an amino acid sequence that is at least 80%, preferably 85%, more preferably 90%, and most preferably 95% identical to a reference amino acid sequence, and which retains the same functional activity as the reference sequence. Identity of amino acid sequences is typically measured using sequence analysis software (e.g., Sequence Analysis Software Package of the Genetics Computer Group, University of Wisconsin Biotechnology Center, 1710 University Avenue, Madison, Wis. 53705).

As used herein, "expansion" or "expanding" of cells means culturing cells for a time and under conditions that allow the cells not only to grow and thrive, but to multiply to obtain a greater number of cells at the end of the expansion than at the beginning of the expansion.

As used herein, a "passage" is the process whereby cells that have reached a given number, or a given density, up to and including or beyond confluence, are detached from the tissue culture vessel, collected in an aggregate, such as a pellet formed by centrifugation, and resuspended in tissue culture medium. The suspension is then distributed to tissue culture vessels, such as plates or flasks, in such a way as to provide the cells with a greater total surface area on which to grow and divide than they had access to previously. This may be done by increasing the number of vessels. For example, the cells growing in one vessel may be detached, collected, resuspended, and distributed to two or more vessels. This process also includes providing the cells with a volume of tissue culture medium that is able to support cellular growth and division.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
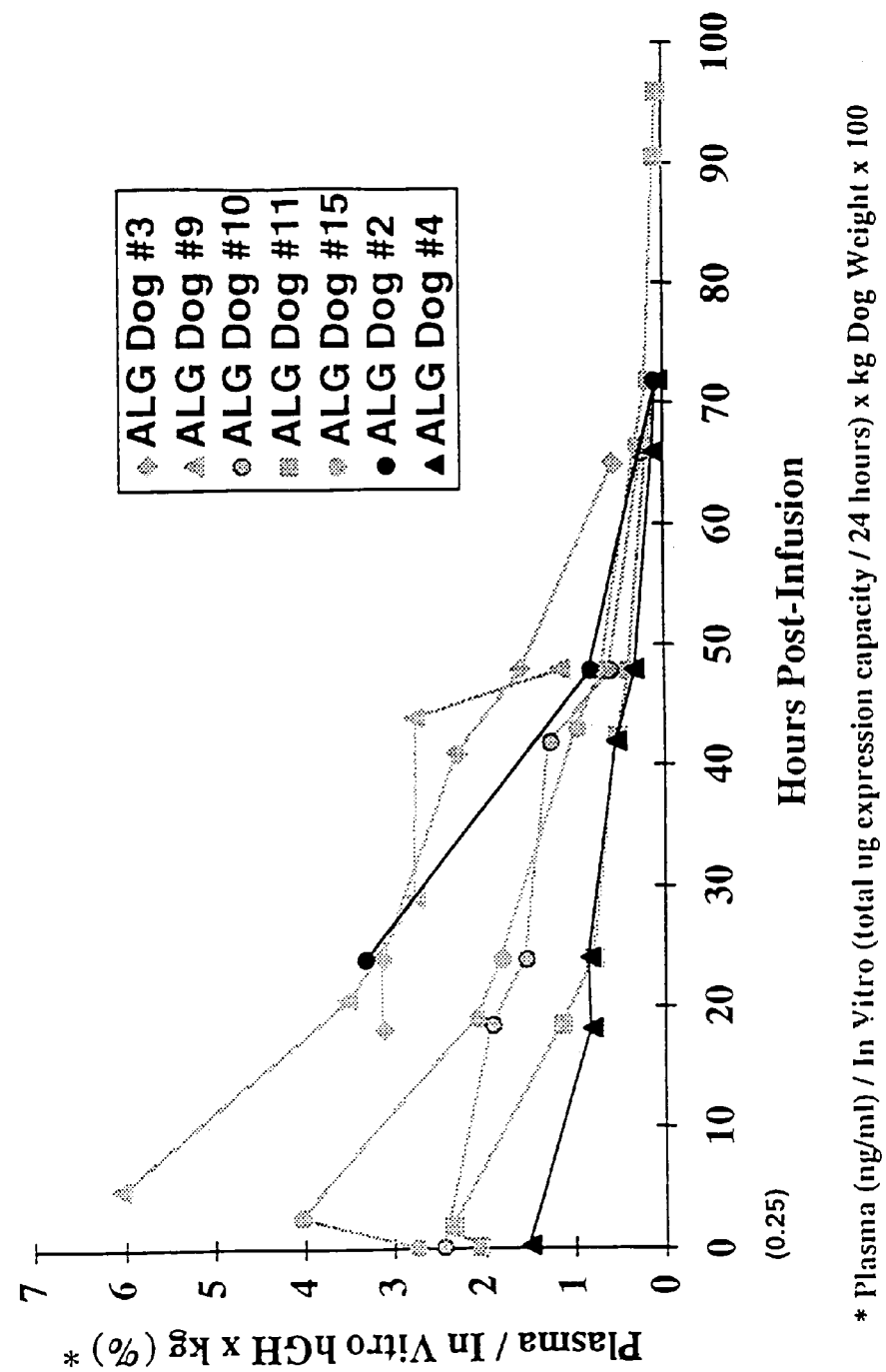
FIG. 1 is a graph depicting the normalized plasma levels in dogs of human growth hormone (hGH) expressed by genetically modified canine bone marrow stromal cells. The cells transplanted into dogs ALG-3, -9, -10, -11, and -15 were not cryopreserved at any stage of preparation. The cells transplanted into dogs ALG-2 and ALG-4 were cryopreserved before they were transfected. Plasma levels of hGH for each data point were determined in quadruplicate.

There now follows a description of methods for obtaining bone marrow stromal cells that are suitable for use in transplantation and gene therapy. These methods include the following steps in various orders: obtaining the cells, expanding the cells in culture, transfecting the cells, and cryopreserving the cells. These examples are provided for the purpose of illustrating the invention and should not be construed as limiting.

Expansion, Transfection, and Cryopreservation of Bone Marrow Stromal Cells

Mongrel dogs were fully anesthetized and whole bone marrow was aspirated aseptically from the iliac crest. The aspirate syringes contained heparin to prevent clotting. The bone marrow was transferred from the syringe to a 50 ml conical tube containing 15 mls of a chilled tissue culture medium, such as RPMI or DMEM, and anti-fungal and antibiotic agents (50 $\mu$g/ml fungizone; 50 $\mu$g/ml gentamicin; 100 units/ml penicillin; 100 $\mu$g/ml steptomycin sulfate). Approximately 10–15 mls of bone marrow aspirate was added to each tube and the mixture was kept on ice. Human bone marrow, e.g., from femoral heads, can be obtained by the same techniques, or by other standard techniques.

Nucleated cells were prepared from the bone marrow samples by a standard Ficoll cushion technique. Briefly, 15 ml of FICOLL-PAQUE™ (Pharmacia Biotech) was placed in a 50 ml conical tube and one half of each of the marrow-medium samples was carefully layered on top of the Ficoll. The samples were centrifuged at 400×g for 30 minutes at 18° C. with the brake off so that the centrifuge head decelerated slowly after the elapsed time. The top layer of the resultant preparation, which contained cell-free medium, was removed and discarded. The middle layer, which contained nucleated cells, was carefully collected and placed into a fresh 50 ml tube containing 20 ml of tissue culture medium, as described above. Additional medium was added to bring the final volume to 50 ml.

The nucleated cells include the bone marrow stromal cells. However, the stromal cells represent only a small fraction, i.e., one in a thousand, of the total number of nucleated bone marrow cells obtained in a bone marrow aspirate.

Expansion

The nucleated cells were collected in a pellet by centrifugation at 100×g for 10 minutes. The cell pellet was washed with tissue culture medium (RPMI or DMEM with fungizone (25 $\mu$g/ml), gentamicin (25 $\mu$g/ml), penicillin (100 units/ml) and streptomycin sulfate (100 Mg/ml)) and resuspended in 5–10 ml of "complete bone marrow stromal cell medium" ("complete medium"). After resuspension the cells were counted.

Generally, the complete bone marrow stromal medium contains the following ingredients in the following ranges of amounts or concentrations. DMEM with 1 to 50% fetal bovine serum (FBS) (preferably greater than 12.5%) by volume; 0.01 to 100 ng/ml of an aFGF polypeptide, e.g., a recombinant aFGF; 0.05 to 100 units/ml of a heparin polypeptide, e.g., sodium heparin; 0.25 to 250 $\mu$g/ml of fungizone; 0.25 to 250 $\mu$g/ml of gentamicin; 1 to 1000 units/ml penicillin; and 1 to 1000 $\mu$g/ml of streptomycin sulfate. As used in the experiments described below, the complete medium contained DMEM with 16 percent by volume heat-inactivated FBS, recombinant aFGF (1 ng/ml) by volume, heparin (5 units/ml), fungizone (25 $\mu$g/ml), gentamicin (25 $\mu$g/ml), penicillin (100 units/ml), and streptomycin sulfate (100 $\mu$g/ml).

Tissue culture flasks (T150 cm$^2$) are preferably coated initially with gelatin and FBS. Specifically, a solution of gelatin (Sigma; 1% in water) was added to each flask until the bottom of the flask was just covered. The excess was removed and the flasks were left undisturbed, bottom side down, at room temperature, for at least 30 minutes. The flasks can be refrigerated at this point for later use. Heat-inactivated FBS was then added to the gelatinized flasks. As before, the excess solution was removed and the flasks were left, bottom side down, at room temperature for at least 30 minutes. The flasks were either used at this point or refrigerated.

The nucleated cells of the bone marrow, prepared as described above, were added to the coated flasks at approximately 1×10$^8$ cells/T150 flask. The cells were incubated in 15 mls of complete bone marrow medium, at 33° C., in the presence of 5% CO$_2$. After 3–4 days, or when the stromal cells have adhered to the inner surface of the tissue culture vessel, 15 ml of complete medium was added to the cultures, dropwise, so the cells were not disturbed. One week later, before vital components within the medium are depleted, the so-called "conditioned medium," i.e., the medium in the flask which contains non-adherent cells, was removed, and 15 ml of fresh complete medium was added to the flask. The non-adherent cells were pelleted by centrifugation at 500×g for 5 minutes, resuspended in 15 ml of conditioned medium and returned to the original flask. Thus, the non-adherent cells were returned to the flask and the medium was changed in such a way that it contained one part fresh medium and one part conditioned medium.

In general, the key to this regimen of cell culture is to: (1) coat the inner surface of the tissue culture vessel with a solution of gelatin, (2) keep returning the non-adherent cells to the culture when exchanging the medium, (3) add medium that contains sufficient nutrients to sustain growth without removing all of the substances secreted by the bone marrow cells, which enhance their growth, (4) supplement the tissue culture medium with aFGF, and (5) supplement the tissue culture medium with heparin.

This process, where the non-adherent cells are removed, pelleted, and returned to the culture with equal parts of fresh and conditioned medium, is repeated once a week, for 2–3 weeks or until a monolayer of adherent cells has formed. Once the monolayer of bone marrow stromal cells developed, the cells were passaged by splitting them 1:2 or 1:3 into fresh flasks. At this point, and from this point on, the flasks were coated with gelatin but not with FBS. It is also no longer necessary to feed the established stromal cells with conditioned medium or to return non-adherent cells to the culture. The cells may be passaged in this manner at least 8 times or more.

This method can be used to select and expand canine or human (or other vertebrate) bone marrow stromal cells, to develop a total cell number of more than $10^8$, and even more than $3 \times 10^9$ in vitro, from bone aspirates of individual subjects. Other techniques of obtaining bone marrow can be used. The bone marrow stromal cells obtained from dogs by this method exhibited the characteristic appearance of fibroblast-like bone marrow stromal cells. Given that the success of gene therapy depends on the cellular production of adequate levels of the transgene product, which can be quite low, the ability to expand cells in culture to $10^8$ to $10^9$ or more represents a substantial improvement.

Transfection

To determine whether bone marrow stomal cells that were grown according to the methods described above could be transfected, the plasmid expression vector pETKhGH was prepared and transfected into canine stromal cells using standard techniques. The dog model is an accepted animal model of the human bone marrow system, and results in dog studies are reasonably predictive of efficacy in human patients.

The vector was prepared from PTKGH (Selden et al., 1986, Mol. Cell. Biol., 6:3173–3179), which is comprised of the human growth hormone (hGH) gene, including introns, under the transcriptional regulation of HSV thymidine kinase (TK) promoter sequences (Nichols Institute Diagnostics, San Juan Capistrano, Calif.). In addition, a 179 base pair FokI-PvuII restriction enzyme fragment from the SV40 enhancer (as described in Hurwitz et al., 1987, Nucl. Acids Res. 15:7137–7153) was tailed with HindIII sites by PCR using a derivative of the pSV(E)-MLP plasmid (Hurwitz et al., supra) as a template, and cloned into the HindIII site of pTKGH just upstream of the TK promoter. The pETKhGH plasmid lacks a eukaryotic origin of replication and does not integrate into the host cell genome. As such, the vector expresses hGH transiently.

By simply varying which gene is incorporated, vectors can be made that would express secreted proteins such as serum proteins, clotting factors, e.g., factor VIII and factor IX, cytokines, lymphokines, growth factors, e.g., human growth hormone, peptide hormones, lipid binding proteins, metabolic enzymes, antibacterial agents, antimicrobial agents, antifungal agents or neurotransmitters. Similarly, the vector could express cell surface components, e.g. receptors or cell surface adhesion molecules such as vascular cell adhesion molecule-1 (V-CAM-1), intercellular adhesion molecule-1 (1-CAM-1), or V-LAM, or secreted gene products, such as collagen.

Methods of engineering plasmid expression vectors are well known to persons of ordinary skill in the art, and many expression vectors that contain genes encoding proteins within the families listed above have been constructed and can be used to transfect bone marrow stromal cells. These include viral vectors that encode cytokines, such as IL-6 (Whartenby, et al., 1995, Pharmacology and Therapeutics, 66:175–190), and IL-7 (Kim et al., 1994, Human Gene Ther., 5: 1457–1466); clotting factors such as factor VIII (Dwarki et al., 1995, Proc. Natl. Acad. Sci., USA, 92:1023–1027), and factor IX (Palmer, et al., 1989; Blood, 73:438–445); metabolic enzymes, such as aspartyl-glucosaminidase (Enomaa et al., 1995, Human Gene Ther., 6:723–731), purine nucleoside phosphorylase (Jorisson et al., 1995, Human Gene Ther., 6:611–623), and uroporphyrinogen III synthase (Moreau-Gaudry et al., 1995, Human Gene Ther., 6:13–20); as well as cell surface adhesion molecules such as I-CAM-1 (Pilewski et al., 1995, AM. J. Resp. Cell. Mol. Biol. 12:142–148). In addition, useful plasmid expression vectors have been constructed for the expression of V-CAM-1 (Lobb et al., 1991, Biochem. Biophys. Res. Comm., 78:1498–1504), and neural cell adhesion molecule (N-CAM; Woo et al., 1993, Exp. Cell Res. 204: 336–345).

In the present example, canine bone marrow stromal cells were transfected with pETKhGH by either the $CaPO_4$-DNA coprecipitation method, using the MBS Mammalian Transfection Kit (Stratagene Cloning Systems, LaJolla, Calif.), or the cationic lipid-DNA complex method using LIPO-FECTAMINE® reagent and OPTI-MEM® I reduced-serum medium (Life Technologies) according to the manufacturer's instruction.

Several batches of expanded stromal cells from a dog designated ALG-2 were transfected with the calcium-phosphate method and one batch of cells from dog ALG-4 was transfected by lipofection. The amount of hGH secreted into the complete medium was measured by a radioimmunoassay during a 24 hour period. These data are shown in Table 1. Cells from dog ALG-2 secreted a total of 1,818 µg of hGH and cells from dog ALG-4 secreted 824 µg of hGH during this time.

In column 7 of Table 1, the hGH expression is based on in vitro expression during the 24 hour period prior to cryopreservation. All cells derived from dog ALG-2 (data in rows 1–5 of Table 1) were transfected with the MBS Mammalian Transfection Kit from Stratagene or ProFection Mammalian Transfection Systems from Promega. The data in the last row, from dog ALG-4-derived cells were transfected with the LIPOFECTAMINE reagent from Life Technologies, Inc.

TABLE 1

Ex Vivo Transfection of
Bone Marrow Stromal Cells with the pETKhGH Plasmid Expression Vector Prior to Cryopreservation

| ALG Dog # (USDA #) | Method of Transfection (Date of Transfection) | Passage # of Transfected Cells | # of Cells Seeded for Transfection/ T150 Flask | # of T1150 Flasks Transfected (& Survive) | # of Cells Recovered and Frozen | hGH Expression (ug/$10^6$ cells/24 hr) | Total hGH Expression Capacity (ug/24 hr) |
|---|---|---|---|---|---|---|---|
| #2 (82716) | Calcium Phosphate (6/18 or 7/6 or 7/10/94) | P11 or P12 | A Collection of 100 mm Dishes and T150 Flasks | A Collection of 100 mm Dishes and T150 Flasks | $8.81 \times 10^7$ | 0.294 | 25.9 |
| | Calcium Phosphate (8/4/94) | P12 | $3.3 \times 10^6$ | 48 | $6.3 \times 10^8$ | 0.198 | 125 |
| | Calcium Phosphate (8/11/94) | P13 | $5 \times 10^6$ | 50 | $1.98 \times 10^9$ | 0.161 | 318 |
| | Calcium Phosphate (8/18/94) | P14 | $5 \times 10^6$ | 18 | $3.39 \times 10^8$ | 0.313 | 106 |
| | Calcium Phosphate (8/11/94) | P15 | $4.9 \times 10^6$ | 42 | $3.14 \times 10^8$ | 3.11 | 1243 |
| | | | | TOTAL | $3.35 \times 10^9$ | | 1818 |
| #4 (89711) | Lipofection (8/25/94) | P3 | $4 \times 10^6$ | 41 | $2.85 \times 10^8$ | 2.89 | 824 |

Cryopreservation

Immediately after the assessment of hGH production, the expanded stromal cells were frozen. In preparation for cryopreservation, the cells were rinsed once with Dulbecco's Phosphate Buffered Saline (Gibco #14190-144) and detached with Trypsin-EDTA (0.05% Trypsin, 0.53 mM tetra-sodium-EDTA; Gibco #25300-062). The trypsinization was stopped by adding an equal volume of media (DMEM with antibacterial and anti-fungal agents at the concentrations given above). The cells were pelleted by centrifugation at 500×g for 5 minutes, resuspended in 3 ml of media, and counted. Cell density was adjusted to $1 \times 10^6$ cells/ml with media containing 10% Dimethyl Sulfoxide (DMSO; Sigma D-8779), and 1 ml aliquots were added to sterile 2 ml cryogenic vials (Corning #25704). The vials were immediately stored at −80° C. overnight. After 24 hours, the vials were transferred to a liquid nitrogen tank or to a −150° C. freezer for long-term storage. $3.35 \times 10^9$ cells derived from dog ALG-2 and $2.85 \times 10^8$ cells derived from dog ALG-4 were cryopreserved in this manner.

For larger scale cryopreservation, after trypsinization, the cells are pelleted by centrifugation at 500×g in larger volumes of medium, e.g., 200 ml or more. The cell pellet is suspended in 10 to 20 ml of medium, and cells are counted. The suspension is then brought to a larger volume, e.g., 45 ml, with medium, and added to a transfer pack container (Baxter Fenwal, 4R2001) with a sterile syringe fitted with an 18 gauge sterile needle. Five ml of DMSO is then added, and the pack is stored at −80° C. overnight. After 24 hours, the pack is transferred to liquid nitrogen tanks or to a −150° C. freezer for long-term storage. Both of these cryopreservation methods can be used for stromal calls from humans as well as from dogs, primates, cows; pigs, and other animals.

Transplantation

Stromal cells that had been modified ex vivo and cryopreserved were later thawed, washed, and re-infused into a foreleg vein of the dogs in an autologous manner. Both animals had previously received autologous infusions of cells that had been cultured but that were not modified with an hGH expression vector. The expression capacity of the cells infused into dog ALG-2 was 1,400 μg hGH/24 hr and, for dog ALG-4, 575 μg hGH/24 hr (Table 2). The expression capacities were determined by the number of cells infused and the level of hGH expression in vitro during the 24 hour period preceding cryopreservation.

The data shown in Table 2 were derived from cells that were reintroduced intravenously into a foreleg vein. The hGH expression capacities, of 1,400 and 575 μg/24 hours, shown in the last column were based on in vitro expression during the 24 hour period prior to cryopreservation. The value of 445 μg/$2^4$ hours, again in the last column, was also based on in vitro expression. In this instance, an aliquot of cells was taken from the pool of cells that were reinfused and returned to tissue culture. hGH was measured during the 24 hour period immediately after the remainder of the cells were reinfused.

Some cells derived from dog ALG-4 were returned to tissue culture, and hGH was measured in vitro for 24 hours after the sibling cells were reinfused. During this time, the cells in culture expressed and secreted 2.24 μg of hGH/$1 \times 10^6$ cells/24 hours, which predicts an in vivo expression capacity of 445 μg of hGH/24 hr period (Table 2). The same measurements were taken before cryopreservation. At that time, the cells in culture expressed and secreted 2.89 μg of hGH/$1 \times 10^6$ cells/24 hours, which predicts an expression capacity in vivo of 575 μg/24 hours. Note that the measurements taken before cryopreservation are very similar to those obtained after cryopreservation.

Normalized plasma levels were also similar whether or not the dogs had previously been infused with autologous bone marrow stromal cells. These data indicate that cryopreservation does not significantly alter the ability of transfected stromal cells to express hGH. Furthermore, these data demonstrate that in vitro expression levels are reliable indicators of the subsequent level of in vivo hGH expression, regardless of whether or not the cells have been cryopreserved. Thus, in vitro levels of hGH expression prior to cryopreservation can be used to determine a therapeutically useful number of cells for transplantation.

Secretion of hGH in vivo, into peripheral blood plasma, continued for 3 days following reintroduction of the modified stromal cells into both dogs ALG-2 and ALG-4, achieving a peak plasma level of 1.76 ng/ml in dog ALG-2 (Table 3).

In Table 3, the lowest hGH standards, shown in column 2, are statistically higher (t-test) than the expression of hGH in pre-infusion plasma at a confidence level of greater than 95%. The average plasma levels of hGH, shown in column 4, represent values that are statistically higher (t-test) than those seen in pre-infusion plasma at a confidence level of greater than 99%, except where indicated. The data above the thick line in Table 3 pertains to ALG-2, and data below the thick line pertains to ALG-4.

were normalized by dividing absolute hGH plasma levels (ng/ml) by the total hGH expression capacity ($\mu$g/24 hr) of the cells infused into each dog, multiplied by the weight (kg) of the individual dog, and then by 100%.

As shown in FIG. 1, data collected from dogs ALG-2 and ALG-4 show the plasma level of hGH in the dogs produced by cells that have been cryopreserved after transfection, and data collected from dogs ALG-3, -9, -10, -11, and -15 show the plasma level of hGH secreted by cells that were infused without being frozen. The results vary from dog to dog, but show that the cryopreserved cells and non-cryopreserved cells worked essentially the same. Thus, these data support the use of cryopreservation as a means to repeatedly transplant ex vivo expanded bone marrow stromal cells.

TABLE 2

Reintroduction into Dogs of Thawed Autologous Bone Marrow Stromal Cells Transfected with the pETKhGH Plasmid Expression Vector Prior to Cryopreservation

| ALG Dog # | Date of Reintroduction of Cells | Method of Reintroduction of Cells | Number of Cells | Cell Conc. (cells/ml) & Volume | Previous Autologous Stromal Cell Infusion? | hGH Expression Capacity (ug/24 hr) |
|---|---|---|---|---|---|---|
| #2 | Sep. 7, 1994 | Intravenous | $2.58 \times 10^9$ | $1.29 \times 10^7$ 200 ml | Yes | 1,400 |
| #4 | May 16, 1995 | Intravenous | $1.99 \times 10^8$ | $1.99 \times 10^6$ | Yes | 575 445 |

TABLE 3

Plasma Levels of hGH Expressed In Vivo by Reintroduced Ex Vivo Modified Autologous Bone Marrow Stromal Cells

| Days (Hours) Following Reintroduction of Cells | Assay Standard Range | Number of Assayed Replicates of Sample | Average Plasma Level of hGH +/− Assay Standard Error |
|---|---|---|---|
| 1 (24 hr) | 0.20–5.0 ng/ml | 5 | 1.76 ng/ml (+/−0.03) |
| 2 (48 hr) | 0.05–5.0 ng/ml | 3 | 0.425 ng/ml (+/−0.013) |
| 3 (72 hr) | 0.05–5.0 ng/ml | 3 | 0.036 ng/ml (+/−0.006)(98%) |
| 4–13 | 0.05–5.0 ng/ml | 4 | Undetectable (i.e., not above background controls at the 95% level) |
| 0 (0.25) | 0.011–1.10 ng/ml | 4 | 0.314 ng/ml (+/−0.009) |
| 1 (18 hr) | 0.011–1.10 ng/ml | 4 | 0.169 ng/ml (+/−0.004) |
| 1 (24 hr) | 0.011–1.10 ng/ml | 4 | 0.174 ng/ml (+/−0.009) |
| 2 (42 hr) | 0.011–1.10 ng/ml | 4 | 0.110 ng/ml (+/−0.009) |
| 2 (48 hr) | 0.011–1.10 ng/ml | 4 | 0.070 ng/ml (+/−0.004) |
| 3 (66 hr) | 0.011–1.10 ng/ml | 4 | 0.021 ng/ml (+/−0.002) |
| 3 (72 hr) | 0.011–1.10 ng/ml | 4 | 0.011 ng/ml (+/−0.001)(98%) |
| 4–7 | 0.011–1.10 ng/ml | 4 | Undetectable (i.e., not above background controls at the 95% level) |

The longest known half-life of hGH is 26 minutes (in normal humans r guinea pigs; Holl et al., 1993, J. Clin. Endocrinol. Metab., 77:216). Assuming that hGH in canine plasma has a similar half-life, any hGH that was present would be reduced to less than 0.01 ng/ml, which is undetectable by radioimmunoassay, in less than three hours. Therefore, the hGH detected in the plasma is the result of de novo expression from reintroduced ex vivo modified bone marrow stromal cells.

Figure 2:
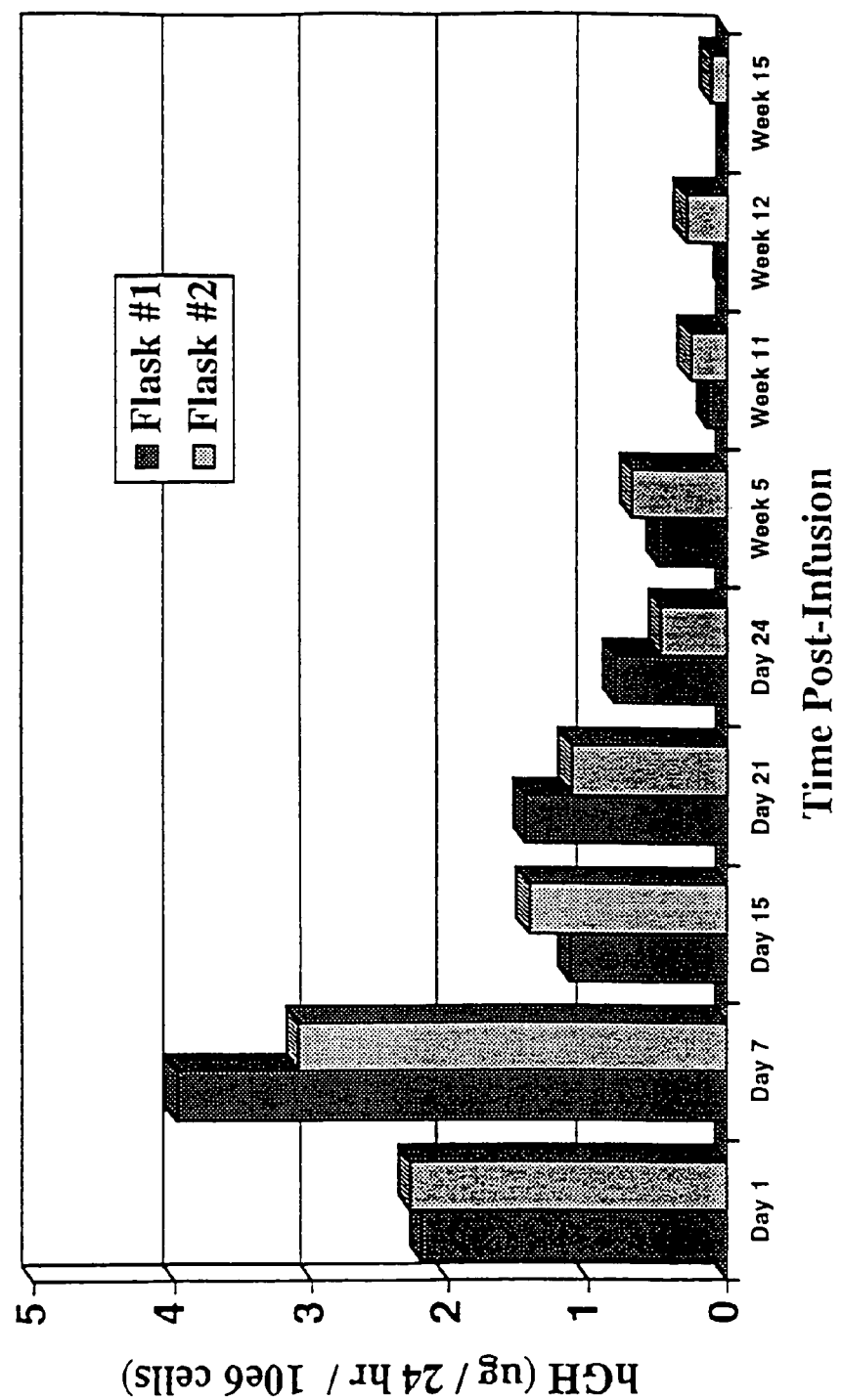
FIG. 2 is a bar graph depicting the expression of hGH in vitro from transfected canine bone marrow stromal cells. These cultures were established from cells from a sample that was expanded, transfected, cryopreserved, and then thawed. The majority of the cells in the sample were autologously transplanted.

In other studies, plasma levels of hGH from transplanted stromal cells that were genetically modified as described here, but that were not cryopreserved at any stage, were determined. The normalized in vivo levels of hGH expression were comparable, whether or not the genetically modified stromal cells were cryopreserved before reinfusion. Levels of hGH in the plasma of each dog, at each time point, Although the majority of the vector-modified cells were used for transplantation, a small number of these cells were returned to tissue culture. Periodically, samples of tissue culture medium that had been conditioned by these cells were assayed for hGH. The cultured cells, which serve as a model for the reintroduced cells, expressed and secreted significant levels of hGH in vitro. Although the level of expression decreased over time, cells were shown to express hGH in vitro for as long as 15 weeks after the time sibling cells were reintroduced to animals (FIG. 2). FIG. 2 shows that the level of hGH peaked at 4 or 3 (flasks 1 and 2, respectively) $\mu$g/24 hr/$10^6$ cells, was still over 1 $\mu$g/24 hr/$10^6$ cells, and then dropped gradually until week 15.

Circulating stromal cells bearing the hGH vector were detected by a sensitive nested PCR assay. This assay can detect 5–10 copies of the pETKhGH plasmid expression vector in a background of 1×10⁵ control stromal cells and is effective in 90% of the reactions performed (9 positives/10 reactions).

In preparation for the nested PCR assay, blood samples were obtained after transfected stromal cells were infused. These samples were subjected to a Ficol gradient and bone marrow stromal cells from the buffy coat fraction were isolated. Cells obtained from the buffy coat of dog ALG-4 prior to the autologous transplantion of stromal cells served as the negative control. Cells obtained from the buffy coat were incubated in cell lysis buffer (1×10⁷ cells/ml) at 55° C., overnight. Lysis buffer is comprised of 50 mM Tris-HCl, pH 8.5, 1 mM EDTA, 0.5% Tween 20 and 200 µg/ml Proteinase K (Boehringer Mannheim Indianapolis, Ind.). Cell debris was removed by centrifugation in an Eppendorf microcentrifuge for 10 minutes. The lysate supernatant was incubated at 95° C. for 10 minutes and subsequently used in PCR experiments.

The nested PCR reaction was performed in two steps. In the first step, 25 µl of cell lysate (2.5×10⁵ cell equivalents) was mixed with 25 µl of 2×PCR reaction mix and subjected to an initial incubation at 94° C. for 5 minutes and then 35 cycles of 94° C. (30 seconds), 58° C. (50 seconds), and 72° C. (1.5 minutes) in the presence of a 5'-oligonucleotide primer that is homologous to exon 2 sequences in the hGH gene, and a 3'-primer that is homologous to exon 5 sequences in the hGH gene. Primers were obtained from Oligos, etc. Inc. (Wilsonville, Oreg.). The final concentration of the PCR reaction mix was 50 mM Tris-HCl (pH 9.0), 50 mM NaCl, 2 mM MgCl₂, 0.2 mM each of NTPs (DATP, dGTP, dCTP, and dTTP), 0.5 µM each of 5'- and 3'-primers, and 0.5 units Taq DNA polymerase (Promega Corp., Madison, Wis.).

For the second nested PCR amplification, 1 µl of the first PCR reaction product was added to 49 µl of 1× PCR reaction mix in the presence of a 5'-primer that is homologous to exon 2 sequences in the hGH gene, and a 3'-primer that is homologous to exon 5 sequences. Importantly, this second set of oligos is homologous to gene sequences internal to the first set of oligos and did not overlap their sequences. All primers were chosen from regions of the template gene that did not contain internally repetitive sequences and that had a G-C content of less than 67%. Numerous other primer combinations can be developed by standard techniques for use in this nested PCR assay.

Thermocycling for the nested reaction was identical to the first reaction except that the annealing temperature was 56° C. A 10 µl aliquot of each of the first and nested PCR reaction products was analyzed by electrophoresis on a 1% agarose gel and the amplified cDNA was visualized by ethidium bromide staining. DNA molecular weight markers were comprised of phiX174 DNA digested with HaeIII (Boehringer Mannheim). The expected size of the correct nested PCR product is 1,119 base pairs. Control analyses on canine cells demonstrated that the nested PCR reaction protocol did not detect canine growth hormone gene sequences.

Nested PCR analysis revealed that vector-modified stromal cells were present in the peripheral circulation of animals for 15 weeks after cells were reintroduced to the circulation.

Figure 3:
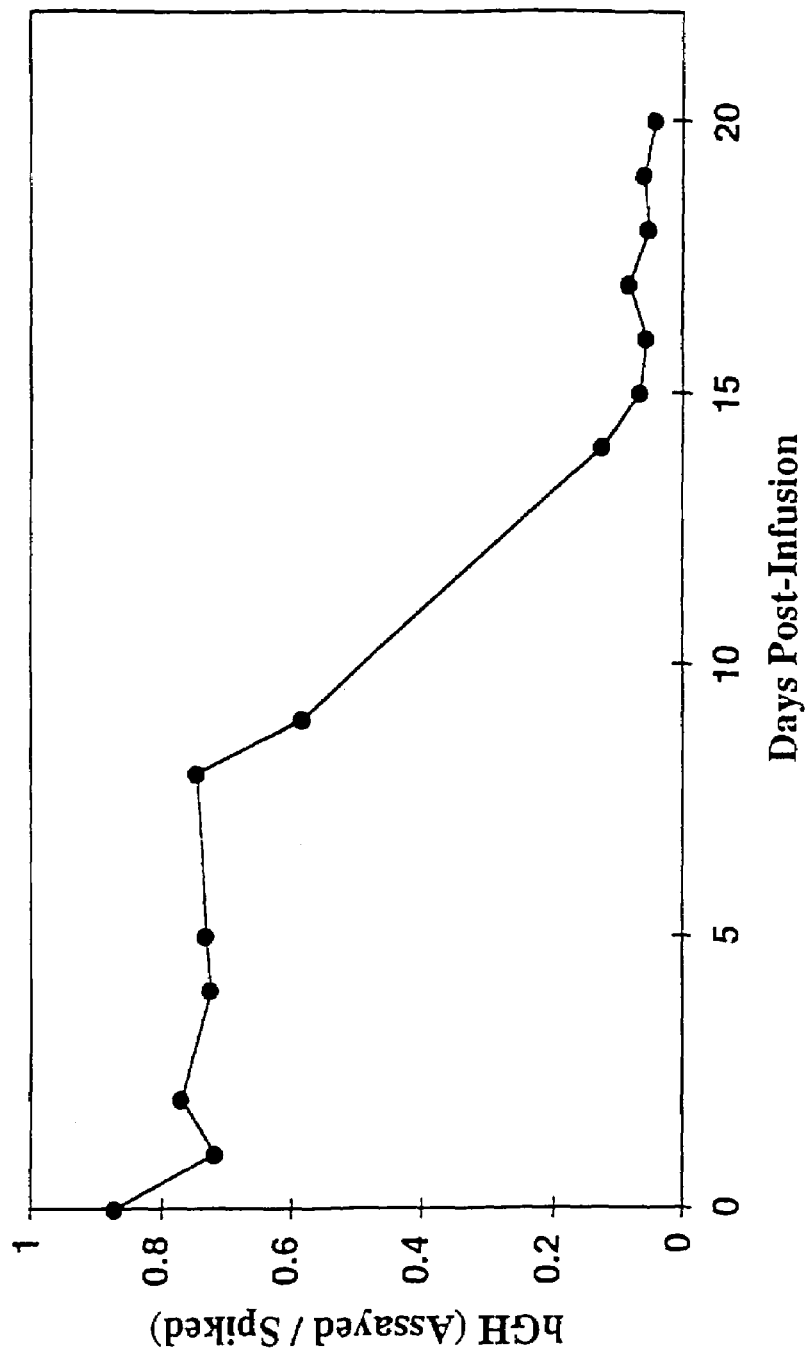
FIG. 3 is a graph that shows the presence of hGH inhibitors in dogs. The inhibitors are shown by comparing the level of hGH assayed by RIA with the amount of hGH "spiked" into the plasma of a dog (ALG-2), over time, following intravenous administration of transfected hGH-expressing stromal cells. Plasma samples were obtained at the times indicated, beginning at day 0. This time point reflects hGH levels in dog plasma "spiked" with 0.5 ng/ml of hGH prior to infusion of the transduced stromal cells. Each sample was assayed in quadruplicate.

Following the reintroduction of hGH-expressing stromal cells, hGH inhibitors developed in vivo (FIG. 3; dog ALG-2). These inhibitors were detected by experiments in which plasma samples were spiked with 0.5 ng/ml of hGH at various times. As shown in FIG. 3, the first hGH measurement (indicated on FIG. 3 as day 0) was obtained prior to infusion of transduced cells. These measurements continued for 20 days following infusion of hGH-expressing stromal cells. Inhibitor activity was determined by comparing the level of hGH in each sample, which was empirically measured by RIA, with the amount of hGH (0.5 ng/ml) purposefully added to each sample.

On days 0 to 8, the percentage of hGH detected was between about 75 (0.75) to 90% (0.9), which served as a control level. Inhibitors in the peripheral blood plasma were evident 9 days after modified stromal cells were reintroduced in vivo and, by 15 days, their level rose to a point sufficient to prevent detection of 93% of the hGH that had been purposefully added to plasma at 0.5 ng/ml. The presence of these inhibitors provides further evidence that the expression vector is producing biologically active hGH.

Expansion, Cryopreservation, and Transfection of Bone Marrow Stromal Cells

In certain-circumstances, it is desirable to expand bone marrow stromal cells in culture and cryopreserve them prior to transduction. To develop such a procedure, bone marrow stromal cells were aspirated from the primary iliac crest of dog ALG-8, and expanded in vitro by culturing methods described in detail above. After the second passage, 2.12×10⁸ cells were cryopreserved in media containing DMSO by the procedure described in detail above. From this frozen stock, 1×10⁸ cells were subsequently thawed and placed in tissue culture as passage 3 cells. After one additional passage, 1.35×10⁸ cells were transduced by transfection with the pETKhGH plasmid expression vector. The level of in vitro expression and secretion of hGH into the tissue culture media was 1.22 µg/1×10⁶ cells/24 hr period, as determined by radioimmunoassay.

These cells (1.11×10⁸ total cells with an hGH expression capacity of 135 µg/24 hr period) were reintroduced into dog ALG-8 by infusion into a foreleg vein (Table 4). Dog ALG-8 had not previously received autologous bone marrow stromal cells. Secretion of hGH into the peripheral blood plasma was demonstrated for 3 days after the cellular infusion and achieved a peak plasma level of 0.24 ng/ml (Table 5). Given that the half-life of hGH in canine plasma should not be more than 26 minutes, any hGH that was present would fall below the level of sensitivity of the radioimmunoassay (0.01 ng/ml) in less than 1.7 hours in this case. In addition, the levels after infusion (e.g. 0.189 ng/ml at 24 hours; Table 5) would be undetectable in less than 2 hours. Therefore, the hGH present in the plasma 3 days after modified stromal cell infusion must be due to de novo expression of hGH by these cells.

The hGH expression capacity shown in Table 4 was based on in vitro expression of hGH during the 24 hour period preceeding cryopreservation. In Table 5, the lowest hGH standards, shown in column 2, are statistically higher (t-test) than the expression of hGH in pre-infusion plasma at a confidence level of greater than 95%. The average plasma levels of hGH, shown in column 4, represent values that are statistically higher (t-test) than those seen in pre-infusion plasma at a confidence level of greater than 99%, except where indicated.

TABLE 4

Reintroduction into ALG of Autologous Bone Marrow Stromal; Cells Transfected with
the pETKhGH Plasmid Expression Vector Subsequent to Cryopreservation

| ALG Dog # (USDA #) | Date of Reintroduction of Cells | Method of Reintroduction of Cells | Number of Cells | Cell Conc. (cells/ml) & Volume | Previous Autologous Stromal Cell Infusion? | hGH Expression Capacity (ug/24 hr) |
|---|---|---|---|---|---|---|
| #8 | (Jan. 23, 1995) | Intravenous | $1.11 \times 10^8$ | $9.65 \times 10^5$ 115 ml | No | 135 |

TABLE 5

Plasma Levels of
hGH Expressed In Vivo by Reintroduced Ex Vivo Modified Autologous Bone Marrow Stromal Cells (ALG-8)

| Days (Hours) Following Reintroduction of Cells | Assay Standard Range | Number of Assayed Replicates of Sample | Average Plasma Level of hGH +/− Assay Standard Error |
|---|---|---|---|
| 0 (0.25) | 0.04–1.0 ng/ml | 4 | 0.240 ng/ml (+/−0.005) |
| 1 (18.5 hr) | 0.04–1.0 ng/ml | 4 | 0.194 ng/ml (+/−0.006) |
| 1 (24 hr) | 0.04–1.0 ng/ml | 4 | 0.189 ng/ml (+/−0.005) |
| 2 (42 hr) | 0.04–1.0 ng/ml | 4 | 0.136 ng/ml (+/−0.002) |
| 2 (48 hr) | 0.03–0.10 ng/ml | 4 | 0.092 ng/ml (+/−0.001) |
| 3 (66.5 hr) | 0.04–0.10 ng/ml | 4 | 0.057 ng/ml (+/−0.003) |
| 3 (72 hr) | 0.03–0.10 ng/ml | 4 | 0.051 ng/ml (+/−0.003) |
| 4–14 | 0.03–0.10 ng/ml | 4 | Undetectable (i.e., not above background controls at the 95% level) |

Figure 4:
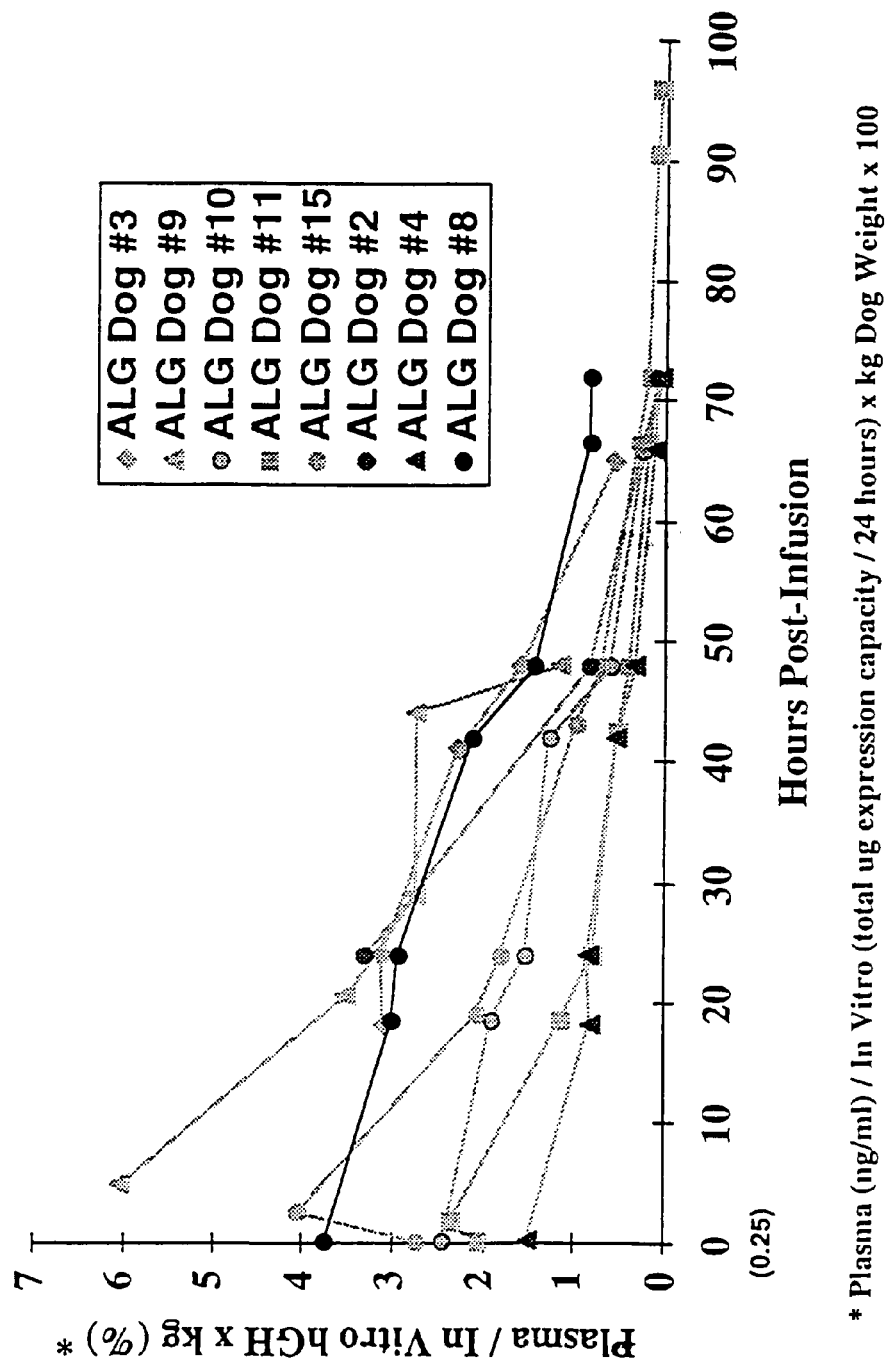
FIG. 4 is a graph showing the normalized plasma level of hGH over time in dogs, following autologous transplantation of bone marrow stromal cells. The cells infused into dogs ALG-3, -9, -10, -11, and -15 were not frozen at any stage of preparation. The cells infused into dogs ALG-2 and ALG-4 were expanded, transfected, and then cryopreserved before they were thawed and transplanted. The cells infused into dog ALG-8 were expanded, cryopreserved, thawed, recultured in vitro, and then transfected before implantation. Plasma levels of hGH for each data point were determined in quadruplicate.

To determine whether cryopreservation prior to transduction affected the ability of the cells to secrete hGH in vivo, normalized plasma levels of hGH were measured from bone marrow stromal cells that had never been cryopreserved (FIG. 4, samples from dogs ALG-3, -9, -10, -11, and 15). These levels were compared with those from stromal cells that were expanded in vitro, cryopreserved, thawed, and transduced with the hGH expression vector prior to reintroduction into animals (dog ALG-8). The normalized in vivo expression levels were comparable, regardless of whether or not the cells had been cryopreserved. Levels of hGH in the plasma of each dog, at each time point, were normalized by dividing absolute hGH plasma levels (ng/ml) by the total hGH expression capacity ($\mu$g/24 hr) of the cells infused into each dog, multiplied by the weight (kg) of the individual dog, and then by 100%. Furthermore, hGH expression was comparable regardless of whether the cells were cryopreserved before (dog ALG-8) or after (dogs ALG-2 and ALG-4) they were genetically modified.

Figure 5:
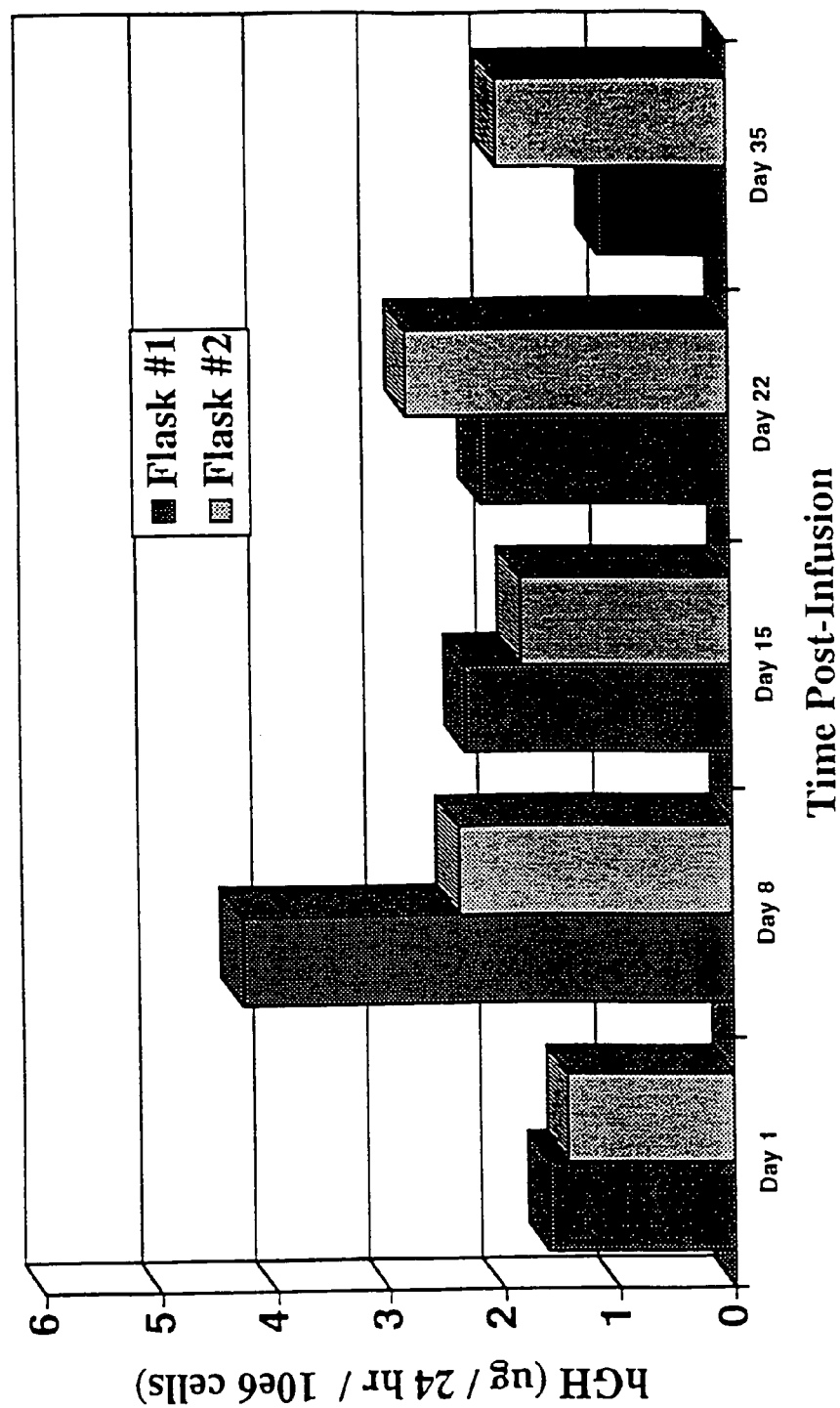
FIG. 5 is a bar graph that shows the level of hGH in samples of stromal cell-conditioned medium in vitro. These cultures were established from cells from a sample that were expanded, cryopreserved, thawed, recultured in vitro, and then transfected. The majority of the cells in the sample were autologously transplanted.

To determine whether the cells transducted and infused to dog ALG-8 maintained the ability to express hGH in vitro, a small number of the cells were kept in culture while the majority of cells were reintroduced into dog ALG-8. Periodically, samples of conditioned medium were assayed for the expression and secretion of hGH and the cells were counted at the time of passage. The cultured cells expressed and secreted significant levels of hGH. Although levels of expression decreased over time, hGH could be detected in vitro for at least 5 weeks after the sibling cells were reintroduced into ALG-8 (FIG. 5).

Plasma levels of hGH were detected in dog ALG-8 as soon as 15 minutes following the infusion of cells. To determine the level of expression of infused cells for this period, a 1 ml aliquot of the modified cells that were intended for reinfusion to ALG-8 was kept on ice while the rest of the cells were infused. Complete medium (5 ml) was added to the aliquot and the cells were kept at 37° C. for 20 minutes. Subsequently the cells were washed, resuspended in tissue culture medium, and the amount of hGH expressed and secreted into the medium was determined at a time that reflected the 15 minute period post-infusion measurement from plasma.

The in vitro expression capacity was 5.58 ng/1$\times 10^6$ cells/15 minutes. Therefore, the 1.11$\times 10^8$ cells that were infused would express 619 ng of hGH/15 minutes. This in turn, corresponds to a plasma concentration of 0.867 ng/ml (for ALG-8; Table 6). This value is 3.6-fold higher than the assayed level of 0.24 ng/ml of hGH in the plasma fifteen minutes following the end of the infusion of the cells (Table 5). This demonstrated that the infused cells express sufficient hGH in 15 minutes to account for the hGH level seen in plasma 15 minutes after infusion. The level assayed in plasma is probably lower than that predicted by in vitro analysis because of distribution within extravascular, as well as intravascular, compartments.

TABLE 6

In Vitro Expression of hGH During a 15 Minute Time Period from a Sample
of ALG Bone Marrow Stromal Cells at Time of Infusion of Sibling Cells

| Determined Expression of hGH ($ng/10^6$ cells/15 min) | Estimated Expression Capacity of Infused Cells ($1.11 \times 10^8$ cells) (ng/15 min) | Estimated Plasma Volume of Dogs | Estimated Plasma Concentration of hGH Due to Expression in 15 min (ng/ml) |
|---|---|---|---|
| 5.58 ng | 619 ng | 714 | 0.867 ng/ml |

Cryopreservation of Primary Bone Marrow and Subsequent Establishment, Expansion, and Transfection of Bone Marrow Stromal Cells Primary bone marrow aspirate was prepared using a Ficoll gradient, as described above. A small aliquot of $1.9 \times 10^7$ cells, which represented about 10% of the total, was cryopreserved. In preparation for cryopreservation, cells were suspended in 50% medium, 50% FBS at a density of $2-5 \times 10^7$ cells/ml. 900 µl of this suspension was aliquoted into 2 ml sterile cryogenic vials (Corning #25704) with 100 µl of DMSO. The vials were stored at −80° C. for 24 hours and then transferred to a −150° C. freezer or to liquid nitrogen tanks for long-term storage. Human primary bone marrow aspirates can be cryopreserved in the same manner. Cryopreserved cells were subsequently thawed and bone marrow stromal cells established and expanded in culture as described above. After the fourth passage, two T25 flasks containing $4 \times 10^5$ stromal cells each were transfected with the pETKhGH expression vector using LipofectAMINE®. Transduced stromal cells expressed and secreted hGH into the media. Two weeks following transfection, hGH was expressed at 143 ng and 155 ng per $1 \times 10^6$ cells per 24 hours in two flasks and expression of hGH continued for 9 weeks.

These results demonstrate that bone marrow stromal cells can be expanded from primary bone marrow aspirates that have been cryopreserved and that these cells can be transduced at a later time and express transgene product.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

The invention claimed is:

1. A method for preserving transfected bone marrow stromal cells (BMSCs) comprising:
   (a) providing BMSCs which have been transfected with an exogenous gene (transfected BMSCs), the level of expression of the exogenous gene of the transfected BMSCs having a predetermined value;
   (b) washing said transfected BMSCs;
   (c) detaching said transfected BMSCs from a tissue culture dish;
   (d) suspending said transfected BMSCs in cryopreservation medium comprising: about 10% dimethyl sulfoxide, about 1–50% fetal bovine serum, and about 89–40% Dulbecco's modified Eagles' medium;
   (e) storing the transfected BMSCs at about −80° C.;
   wherein said transfected BMSCs in the thawed state have a level of expression of the exogenous gene which is at least about 77% of said predetermined value.

2. The method of claim 1, further comprising:
   (f) thawing the cryopreserved transfected BMSCs.

3. The method of claim 1 wherein said cryopreservation medium comprises about 12.5–50% fetal bovine serum and about 77.5–40% Dulbecco's modified Eagles' medium.

4. The method of claim 3 wherein said cryopreservation medium comprises about 16% fetal bovine serum and about 74% Dulbecco's modified Eagles' medium.

5. The method of claim 1, wherein the bone marrow stromal cells are obtained from bone marrow from a vertebrate.

6. The method of claim 1, wherein the bone marrow stromal cells are obtained from bones removed from a vertebrate.

7. The method of claim 1, wherein the bone marrow stromal cells are mammalian.

8. The method of claim 7, wherein the bone marrow stromal cells are human.

9. The method of claim 7, wherein the bone marrow stromal cells are canine.

10. The method of claim 1, wherein the exogenous gene encodes a secreted peptide.

11. The method of claim 10, wherein the secreted peptide is a serum protein, a blood clotting factor, a cytokine, a lymphokine, a growth factor, a peptide hormone, a lipid binding protein, a metabolic enzyme, an antibacterial peptide, an antimicrobial peptide, an antifungal peptide, or a neurotransmitter.

12. The method of claim 11, wherein the blood clotting factor is factor VIII or factor IX.

13. The method of claim 1, wherein the exogenous gene encodes a cell surface molecule.

14. The method of claim 13, wherein the cell surface molecule is V-CAM-1, I-CAM-1, N-CAM, or V-LAM.

* * * * *